United States Patent [19]

Tremulis et al.

[11] Patent Number: 4,846,193

[45] Date of Patent: Jul. 11, 1989

[54] EXTENDABLE GUIDE WIRE FOR VASCULAR PROCEDURES

[75] Inventors: William S. Tremulis, Redwood City; Ray R. Beitelia, Santa Clara, both of Calif.

[73] Assignee: Advanced Cardiovascular Systems, Inc., Mountain View, Calif.

[21] Appl. No.: 98,990

[22] Filed: Sep. 21, 1987

[51] Int. Cl.⁴ .................... A61M 25/00; A61B 5/00
[52] U.S. Cl. ..................................... 128/772; 604/95; 128/657
[58] Field of Search ............... 604/95, 17 D, 264; 128/656–658, 772

[56] References Cited

U.S. PATENT DOCUMENTS

| 3,631,848 | 1/1972 | Muller | 128/657 |
| 4,619,274 | 10/1986 | Morrison | 128/772 |
| 4,719,924 | 1/1988 | Crittenden et al. | 128/772 |

Primary Examiner—Dalton L. Truluck
Attorney, Agent, or Firm—Fulwider, Patton, Rieber, Lee & Utecht

[57] ABSTRACT

An extendable guidewire and method for introducing and exchanging catheters in vascular procedures such as coronary angioplasty, angiography, and valvuloplasty. The guidewire has first and second interfitting sections movable between extended and retracted positions relative to each other and means to releasably secure the two sections in the extended position.

12 Claims, 1 Drawing Sheet

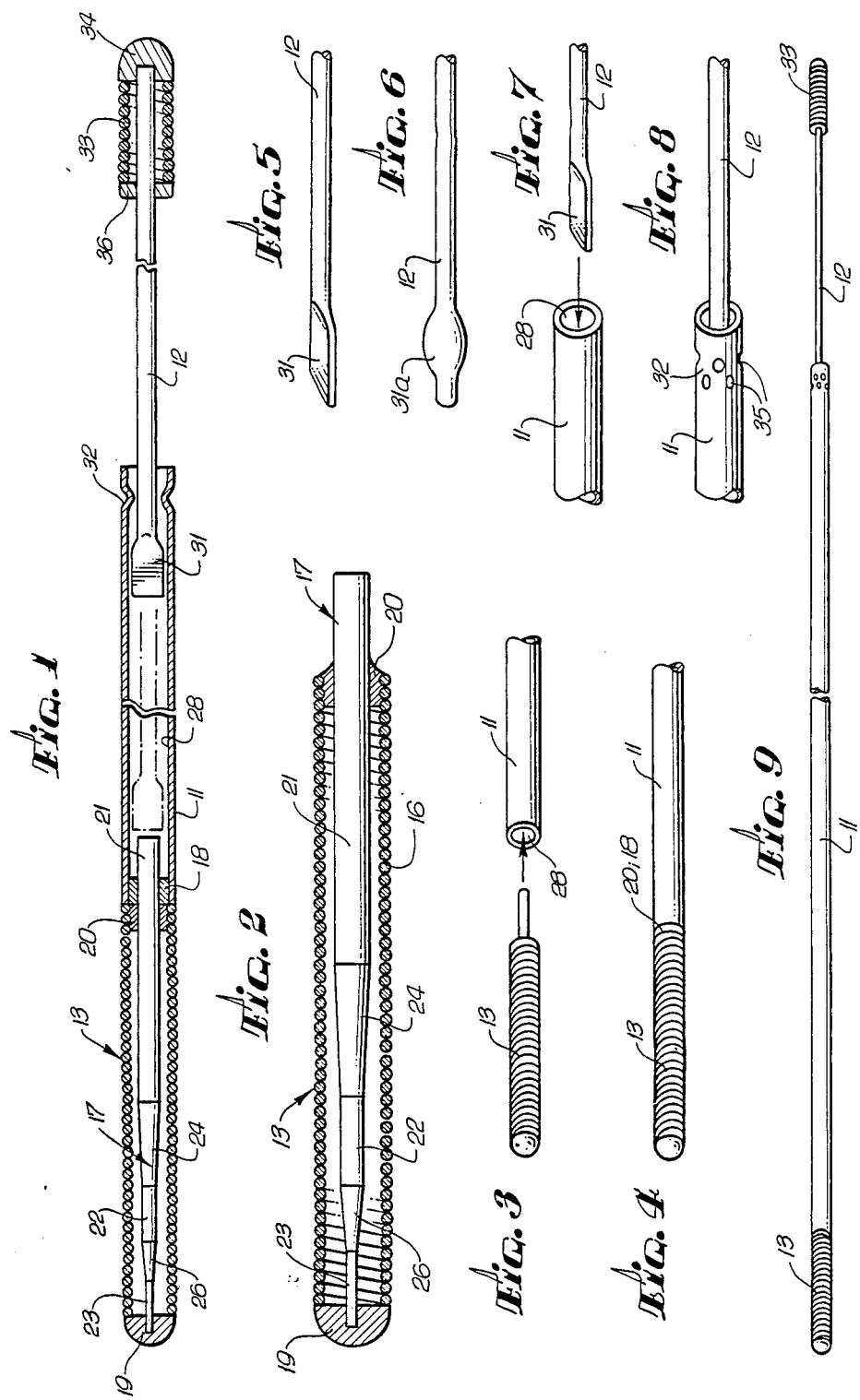

EXTENDABLE GUIDE WIRE FOR VASCULAR PROCEDURES

BACKGROUND OF THE INVENTION

This invention generally relates to guidewires for use in vascular procedures such as angioplasty, angiography, and valvuloplasty, and more particularly to a telescoping guidewire and the methods of using the same in such procedures.

Guidewires are currently used to facilitate the placement of catheters in the arterial system of a patient for cardiovascular procedures such as coronary angioplasty, angioigraphy, and valvuloplasty. The guidewire is typically on the order of 20–50 cm longer than the catheter to permit the guidewire and the catheter to be advanced relative to each other as they are steered into position in the patient's body.

In order to change catheters, the guidewire is generally removed from the patient's vascular system an exchange wire is inserted in its place, the existing catheter is removed and a new catheter is steered over the exchange wire to its proper position, the exchange wire is removed, and the guidewire repositioned with the new catheter. The exchange wire is substantially longer than the guidewire, and it generally extends outside the patient's body for a distance greater than the length of the catheter. With a dilatation catheter having a length on the order of 120–140 cm, for example, a guidewire might have a length on the order of 175 cm, and an exchange wire might have a length on the order of 300 cm. The use of an exchange wire has the obvious disadvantage that it adds extra steps to the procedure. In addition, it requires the doctor to have an additional wire for this purpose.

What has been needed and heretofore unavailable is a system which eliminates the need for an exchange catheter without complicating the catheter exchange procedure. The present invention satisfies this need.

SUMMARY OF THE INVENTION

In general this invention provides a new and improved guidewire for vascular procedures such as coronary angioplasty, angiography, and valvuloplasty which has a telescoping section which facilitates adjustment of the guidewire between extended and retracted lengths and which can be utilized both in the placement of catheters and in the exchange of one catheter for another without removing the guidewire from the patient's vascular system.

In accordance with the invention, a guidewire is provided with first and second telescopically extendable sections movable between axially extended and retracted positions and having means for releasably securing the two sections in the extended position to facilitate the exchange of catheters. The guidewire is positioned within the vascular system of a patient with the two telescoped sections in their retracted position, and a first catheter is advanced along the wire to a desired position in the patient's body. When the first catheter is to be replaced, the guidewire is extended without disturbing the tip portion of the wire within the patient. The first catheter is then withdrawn from the body over the extended guidewire, and a second catheter is inserted into the body over the extended wire. The guidewire may then returned to its retracted position. Thus, there is no need for replacing the guidewire during these procedures. These and other advantages of the invention will become more apparent from the following detailed description of the invention and the accompanying exemplary drawings.

BRIEF DESCRIPTION OF THE DRAWINGS

FIG. 1 is a centerline sectional view of a telescoping guidewire embodying features of the invention;

FIG. 2 is an enlarged centerline sectional view of the flexible tip section of the embodiment shown in FIG. 1;

FIGS. 3–8 are fragmentary side elevational views illustrating several methods of assembling a telescoping guidewire according to the invention; and FIG. 9 is a fragmentary side elevational view of the embodiment shown in FIG. 1.

DETAILED DESCRIPTION OF THE INVENTION

As illustrated in FIG. 1, the telescoping guidewire 10 which embodies features of the invention comprises an outer tubular member 11, an inner shaft or wire 12, and a distal tip section 13. Shaft 12 is telescopically mounted within tubular member 11 for axial movement between axially extended and retracted positions.

Tip section 13 comprises a relatively flexible spring coil 16 and a core wire 17. The spring coil 16 extends axially from the distal end of tubular member 11 for a distance on the order of 30–40 cm for cardiovascular procedures and has an outer diameter which is approximately equal to the outer diameter of the tubular member 11. The core wire 17 extends axially within the spring coil 16 and projects from the proximal end of the coil by a relatively short distance, e.g., 1–5 cm for cardiovascular procedures. The projecting portion of core wire 17 extends into the distal portion of tubular member 11 and is affixed thereto by suitable means such as by soldering as shown at 18. A rounded tip 19 is formed at the distal end of the spring coil 16 by suitable means such as a bead of solder. At least a portion of the spring coil 16 is preferably fabricated of a radiopaque material such as platinum so that it can be observed with a fluoroscope. The proximal end of the spring coil 16 is affixed to the core wire 17 by suitable means such as soldering, as indicated by the reference numeral 20.

In the embodiment illustrated in FIGS. 1 and 2, the core wire 17 of the tip section 13 decreases in cross-sectional extent and increases in flexibility toward the distal end of the wire. The particular core wire 17 shown has a proximal end portion 21 of slightly smaller diameter than the inner diameter of tubular member 11, a central portion 22 of small diameter than the proximal end portion, and a flattened distal end portion 23, with tapered sections 24, 26 between the other portions. The flattened distal end portion 28 of the core wire extends into the rounded tip 19 at the distal end of the spring coil 16 and is affixed thereto. It will be understood, however, that core wire 17 can have any suitable configuration desired and that it can terminate prior to tip 19, if desired. The core wire can be fabricated of any suitable material such as stainless steel.

Tubular member 11 has an outer diameter and a length corresponding to the dimensions of the catheters with which is is to be used. For dilatation catheters having a length on the order of 120–140 cm, for example, the tubular member 11 may have a length on the order of 145 cm. The diameter of the tubular member 11 depends upon the type of procedure in which the guidewire will be used. For angioplasty, the tubular member 11 may typically have a diameter on the order of 0.010–0.018 inch, and for angiography or valvuloplasty, it typically has a diameter on the order of 0.018–0.045 inch. The tubular member 11 has a wall thickness on the order of 0.002 inch and an axially extending lumen 28 with a diameter on the order of 0.006 inch smaller than the outer diameter of the tube. Thus, for example, a 0.018 inch tube might have a lumen with a diameter on the order of 0.012 inch, and a 0.014 inch tube might have a lumen diameter on the order of 0.008 inch. The tubular member 11 is fabricated of a suitable material such as a hollow stainless steel tube commonly known as hypodermic or "hypo" tubing. The tubing preferably has a coating of a lubricious material such as Teflon or Micro Glide TM.

The length of shaft 12 corresponds approximately to the length of tubular member 11 and the diameter of the former slightly smaller than the inner lumen of the latter so that the shaft 12 can slide freely within the lumen 28 of the tubular member 11 between the retracted position shown in phantom in FIG. 1 and the extended position shown in full line. For example, with a tubular member 11 having a length of 145 cm and a lumen diameter 28 on the order of 0.012 inch, the shaft 12 may have a diameter on the order of 0.010 inch and a length that provides the guidewire 10 with an overall length on the order of 300 cm in the extended position. The shaft 12 is thus movable between a retracted position in which the majority of the shaft 12 is within the tubular member 11 and an extended position in which the majority of the shaft 12 projects from the proximal end of the tubular member 11.

Means are provided for releasably securing the shaft 12 in the extended position. This means may include, for example, as shown in FIG. 1, an area 31 of increased lateral dimension toward the distal end of the shaft 12 and an area 32 of decreased lateral dimension toward the proximal end of the tubular member 11. The area 31 of increased lateral dimension may be formed by flattening the distal end portion of the shaft 12, as illustrated in FIG. 5, or by building up the distal end portion with a material such as solder, as indicated in FIG. 6. The area 32 of decreased dimension can be formed by crimping or dimpling the proximal end portion of the shaft 11 or by reducing the inner diameter of the tubular member, e.g., by swaging. Good results have been obtained with inwardly projecting dimples 35 spaced 10 degrees apart around the inner circumference of tube 11. The relative diameters of the enlarged area 31 and the reduced area 32 are such that the shaft 12 and the tubular member 11 are locked together by a friction fit between these two areas. With a shaft 12 having a diameter of 0.010 inch, for example, the distal end portion can be flattened to a width on the order of 0.011 inch or built up to a diameter on the order of 0.011 inch, and the proximal end portion of the tubular member 11 can be crimped to leave an opening of about 0.0102 inch between the inner ends of the dimples 35. This permits the shaft 12 to move freely between the extended and retracted positions, while permitting the shaft 12 to be secured in the extended position but readily released therefrom. The enlarged area 31 and reduced area 32 also prevent the shaft 12 from being withdrawn completely from the tubular member 11. Several areas of friction fit can be provided along the length of the interior of tubular member 11, if desired to provide several secured extruded positions.

A handle 33 is mounted on the proximal end portion of shaft 12 and, as shown in FIG. 1, may comprise a coil which is affixed to the shaft by soldering the proximal and distal ends of the coil to the shaft, as indicated by reference numerals 34, 36. The solder bead 34 at the proximal end of 33 is rounded to form a smooth proximal tip for the wire. The handle preferably has a diameter about the same as the outer diameter of tubular member 11 and a length on the order of about 3 cm. If desired, the handle 33 can be formed of another suitable material such as shrink tubing or any other material which can be affixed to the shaft to facilitate gripping the same.

FIGS. 3–9 illustrate several methods of manufacturing the telescoping guidewire in which tip section 13 is assembled with core wire 17 extending from the proximal end of coil 16. A piece of hypo tubing is cut to the desired length (e.g., 145 cm) for tubular member 11 and the ends thereof deburred. The tubular member is then ground to the desired diameter (e.g. 0.0175 inch) and is coated with a material having a low coefficient of friction. The core wire 17 projecting from the proximal end of the tip assembly 13 is inserted into the distal end of the lumen 28 in the tube 11, as shown in FIG. 3, and is soldered to the tubing 11 at 18 to bond the tip assembly 13 to the tubular member 11. The spring coil 16 is bonded to the wire 17 at 19 and 20 as shown in FIGS. 1 and 4.

The distal end of a shaft 12 is preferably flattened as shown in FIG. 5 or built up as shown in FIG. 6 to the desired dimension (e.g., 0.011 inch) to form enlarged area 31. Thereafter the distal end of shaft 12 is inserted into lumen 28. The proximal end portion of the tubular member 11 is then crimped at 32 to form the area of reduced diameter 32 which cooperates with the enlarged distal end portion 31 of the shaft 12 to releasably secure the shaft 12 in the extended position and should prevent it from being withdrawn completely from the tubular member 11. The shaft 12 is then cut to the extent necessary so that the guidewire 10 will have a desired overall length of 300 cm in the extended position. A handle 33 is mounted on the proximal end of the shaft 12 in any suitable manner.

The operation and use of the telescoping guide wire 10 in accordance with the invention generally is as follows. It is assumed that the catheter is of the balloon dilation type and that it has a hemostatic side arm adapter with a guidewire portion at its proximal end. It is also assumed that the catheter and the dilation system have been purged of air and otherwise prepared for use. If desired, the tip section 13 of the guidewire can be shaped or bent to a desired configuration to facilitate navigation through the coronary anatomy.

A guidewire 10 is inserted through the hemostatic side arm adapter and into the guidewire portion of the catheter. With the guidewire 10 in its retracted position, it is advanced through the introducer and the guidewire lumen of a dilatation catheter until the wire tip is just proximal to the catheter tip. The introducer is then removed by withdrawing it over the guidewire, and the valve which seals the guidewire 10 is closed so that the valve seats around the wire 10 but does not inhibit intentional axial movement thereof.

The dilatation catheter and the guidewire 10 are introduced into the patient through a guiding catheter. With the guiding catheter positioned in the coronary ostium, the dilatation catheter is advanced so that it is just proximal to the tip of the guiding catheter. If desired, a torquing device can be attached to the proximal end portion of the guidewire to facilitate manipulation of the guidewire.

The tip 19 of the guidewire is advanced beyond the distal end of the dilatation catheter while holding the dilatation catheter in place. As the guidewire 10 is advanced, it is rotated and steered into the selected artery. The guidewire tip is preferably advanced through the stenotic area and beyond it, if possible. This permits the balloon portion of the dilatation catheter to be positioned over a more supported section of the guidewire within the lesion. The placement of the guidewire 10 is monitored by observing the position of radiopaque spring coil 16 with a fluoroscope. Once the guidewire is in position, it is held in place and the dilatation catheter is advanced along it into the lesion.

To exchange catheters, the guidewire is extended by withdrawing shaft 12 from tubular member 11 while holding the tubular member 11 in place. The distal portion of the guidewire thus remains in the coronary anatomy and the proximal portion extends outside the patient's body. The shaft is extended until the enlarged distal end portion 31 of the shaft 12 engages the portion 32 of the tubular member 11 which is reduced in diameter to releasably lock the two members together. With the tip of the guidewire still positioned in the coronary anatomy, the torquing device is removed from the proximal end of the guidewire 10, and the dilatation catheter is withdrawn from the patient's body over the extended length of shaft 12 of the guidewire 10.

The new dilatation catheter is prepared in the conventional manner, then advanced over the extended wire 10 and into the patient's body until the balloon crosses the lesion. The guidewire 10 is then returned to its retracted length by grasping the sections 11 and 12 of the wire 10 close to the connection and reinserting the shaft 12 into the tubular member.

The guidewire 10 can be extended and retracted as many times as necessary by following the steps discussed above.

The invention has a number of important features and advantages. The wire can be extended from a standard guidewire length to an exchange wire length by simply pulling the inner shaft out from the main body of the wire, thereby permitting a dilatation catheter to be easily removed and replaced during an exchange procedure without removal of the guidewire and insertion of an exchange wire. When the wire is fully extended, the friction fit between the extendable shaft and the main body of the wire provides a secure connection. When the exchange procedure is completed, the shaft can be retracted to facilitate manipulation of the guidewire within the coronary anatomy.

It is apparent from the foregoing that a new and improved telescoping guidewire and method of manufacturing and using the same have been provided. While only preferred embodiments adapted for use in cardiovascular procedures such as angioplasty, angiography, and valvuloplasty have been described herein in detail, it will be apparent to those familiar with the art that certain modifications and improvements can be made without departing from the scope of the invention as defined by the following claims.

What is claimed is:

1. An extendable guidewire for use in vascular procedures, comprising a first elongated member having proximal and distal ends, an inner lumen extending therein to the proximal end and a flexible coil disposed about the distal end thereof, a second elongated member having proximal and distal ends which is slidably disposed within the inner lumen of the first elongated member and movable therein between extended and retracted positions, and means for releasably securing the second elongated member to the first elongated member when extended out of the proximal end of the first elongated member.

2. The extendable guidewire of claim 1 wherein the first elongated member is of tubular construction.

3. The extendable guidewire of claim 2 wherein the second member is an elongated shaft adapted to fit into the first elongated member.

4. The extendable guidewire of claim 3 wherein the means for releasably securing the shaft of the second elongated member within the inner lumen of the first elongated member in the extended position comprises a shaft section of the second elongated member having an increased lateral dimension toward the distal end thereof, and a section of the first elongated member having a decreased internal lateral dimension toward the proximal end thereof.

5. The extendable guidewire of claim 4 wherein the distal end of the shaft is flattened to form the section of increased lateral dimension.

6. The extendable guidewire of claim 4 wherein the section of increased lateral dimension comprises a body of solder is bonded to the distal end of the shaft.

7. The extendable guidewire of claim 4 wherein a section toward the proximal end of the first elongated member is crimped to reduce the internal lateral dimension thereof.

8. A method of assembling an extendable guidewire for use in vascular procedures, comprising the steps of:
   (a) affixing a flexible tip to the distal end of a tubular member having an axially extending lumen;
   (b) inserting the distal end portion of an elongated shaft having a lateral dimension larger than the remainder of the shaft into the lumen of the tubular member; and
   (c) decreasing the lateral dimension of the lumen toward the proximal end of the tubular member to a dimension slightly less than the larger lateral dimension of the shaft so that the shaft can move freely within the lumen between axially extended and retracted positions with the portions of increased and decreased lateral dimension being frictionally engageable with each other to releasably secure the shaft in the extended position within the tubular member.

9. The method of claim 8 wherein the distal end portion of the shaft is flattened to increase the lateral dimension thereof.

10. The method of claim 9 wherein solder is bonded to the distal end portion of the shaft to increase the lateral dimension thereof.

11. The method of claim 8 wherein the hollow tubular member is crimped in the proximal end thereof to decrease the lateral dimension of the lumen.

12. A vascular procedure utilizing a guidewire comprising a first elongated member having proximal and distal ends, an inner lumen extending therein to the proximal end and a flexible coil disposed about the distal end thereof and a second elongated member slidably disposed within the inner lumen of the first member which is movable between axially extended and retracted positions relative to each other and having means to releasably secure the second member in the extended position, the procedure comprising the steps of:
 (a) positioning the guidewire in a patient's vascular system with the first and second members in their retracted position and the distal end of the the first member being positioned in a desired location;
 (b) advancing a first catheter along the guidewire to a desired position in the patient's vascular system;
 (c) extending the second member of the guidewire out of the proximal end of the first member and releasably securing the second member in that extended position with respect to the first member without disturbing the location of the distal end of the first member within the patient's vascular system;
 (d) withdrawing the first catheter from the patient's body over the extended guidewire and removing the catheter from the guidewire;
 (e) introducing a second catheter into the patient's vascular system over the extended guidewire; and
 (f) returning the second member of the guidewire to its retracted position within the inner lumen of the first member.

* * * * *